United States Patent [19]
Polak

[11] Patent Number: 4,872,872
[45] Date of Patent: Oct. 10, 1989

[54] MEDICAMENT CONTAINER/DISPENSER ASSEMBLY

[76] Inventor: Robert B. Polak, 160 Kimberly Ave., Asheville, N.C. 28804

[21] Appl. No.: 910,407

[22] Filed: Sep. 22, 1986

[51] Int. Cl.$^4$ .............................................. A61M 5/14
[52] U.S. Cl. ..................................... 604/405; 604/87; 604/67; 215/32; 215/261
[58] Field of Search ....................... 604/66, 67, 82, 87, 604/89, 92, 141, 405, 406, 408, 410, 414, 416, 126; 215/32, 248, 249, 250, 261; 220/265

[56] References Cited

U.S. PATENT DOCUMENTS

| | | | |
|---|---|---|---|
| 2,275,567 | 3/1942 | Smith | 604/416 |
| 2,318,379 | 5/1943 | Davis et al. | 215/32 |
| 2,721,552 | 10/1955 | Nosik | 128/272 |
| 2,854,977 | 10/1958 | McConnaughey | 604/416 |
| 3,128,917 | 4/1964 | Krause | 604/92 |
| 3,157,481 | 11/1964 | Bujan | 604/405 |
| 3,206,080 | 9/1965 | Scislowicz | 604/92 |
| 3,881,640 | 5/1975 | Noble | 604/405 |
| 4,029,094 | 6/1977 | Winicki | 604/67 |
| 4,356,012 | 10/1982 | Hofstetter | 604/405 |
| 4,415,393 | 11/1983 | Grimes | 604/403 |
| 4,432,760 | 2/1984 | Mittleman et al. | 604/405 |
| 4,506,793 | 3/1985 | MacGregor et al. | 215/32 |
| 4,583,971 | 4/1986 | Bocquet et al. | 604/82 |
| 4,606,734 | 8/1986 | Larkin et al. | 604/414 |
| 4,614,515 | 9/1986 | Tripp et al. | 604/403 |
| 4,675,017 | 6/1987 | Sato | 604/405 |
| 4,675,019 | 6/1987 | Bellhouse et al. | 604/408 |

FOREIGN PATENT DOCUMENTS 2006712  5/1979  United Kingdom ................. 215/32

Primary Examiner—Stephen C. Pellegrino
Assistant Examiner—Ralph Lewis
Attorney, Agent, or Firm—Klauber & Jackson

[57] ABSTRACT

A medicament container/dispenser assembly includes a substantially non-collapsible main body defining a chamber for containing the medicament in liquid form, the main body having an upper portion and a lower portion; an opening formed in the upper portion; a liquid impervious, gas permeable membrane secured to the upper portion of the main body in sealing relation to the opening; a rupturable exit port formed in the lower portion of the main body. The assembly may also include a second opening formed in the upper portion of the main body in spaced relation to the first-mentioned opening and an elastomeric, puncturable, sealing material secured to the upper portion of the main body in sealing relation to the second opening. In a further embodiment, a conduit may be positioned adjacent the membrane at the upper section of the main body, and may contain a blower for supplying forced air to the membrane through the conduit. A sensing device for sensing flow of the liquid medicament from the exit port and for controlling the blower in response thereto may be associated with the blower, in order to selectively activate the blower to maintain a substantially constant flow of medicament from the exit port.

13 Claims, 2 Drawing Sheets

MEDICAMENT CONTAINER/DISPENSER ASSEMBLY

BACKGROUND OF THE INVENTION

This invention relates generally to medicament containers/dispensers such as intravenous bags, bottles or the like, more particularly, is directed to such devices as are prepared and used for the intravenous delivery of medicaments in pre-measured dosages.

It is estimated that over 675 million intravenous (IV) containers are sold, and that about 240 million intravenous (IV) unit doses of various medicaments or drugs are given annually in the United States. In the past, most of these doses have been prepared under sterile conditions in hospital pharmacies. Recently, however, a number of pharmaceutical manufacturers have been producing and selling some of the more popular drugs in small pre-mixed IV bags, typically in sizes of 50 cc and 100 cc. Because of the overall labor savings, economy and ease of use, these products have gained in popularity, and sales thereof have increased dramatically.

Generally, the pliable IV bags are difficult to manipulate when full, while the rigid glass IV bottles are undesirably breakable. Further, although the IV bags are generally suitable for drugs which are stable at room temperature when pre-mixed, unstable drugs cannot be contained in pre-mixed forms in such IV bags. To overcome this problem, some of these products are being packaged and sold in frozen form, or alternatively, in a double bag configuration in which the contents of one IV bag can be released into the contents of the other IV bag to mix the components at a subsequent time. As will be appreciated, such double bag configuration is relatively expensive and cumbersome to manufacture and use. In an alternative system, the IV bag is provided with a vial port for receiving a drug containing vial which is screwed thereinto. This IV bag with a separately packaged drug vial also is relatively expensive and cumbersome to use.

U.S. Pat. No. 3,059,643 to Barton discloses an arrangement in which a first bottle is provided with a resealable elastic membrane. Another bottle has a bottle adapter with a conduit having a spike at the end, which can be used to puncture the resealable membrane of the first bottle to mix the contents of the two bottles. See also U.S. Pat. No. 4,475,914 to Portnoff. These Patents are particularly useful when mixing unstable drugs.

U.S. Pat. No. 2,275,567 to Smith discloses an arrangement in which an assembly is provided at an inlet of the container, the assembly including a capsule. A rod is positioned in the assembly immediately above the capsule and when depressed, crushes the capsule to release the contents thereof into the contents already in the container, so as to mix the two drugs. However, in this arrangement, the fragments of the capsule also fall into the liquid, and may contaminate the same or obstruct any exit of the mixed drug from the container. In a similar context, U.S. Pat. No. 2,854,977 to McConnaughey discloses an elongated tube with a tapering nozzle, such tube being disposed with flexible walls permitting compression to rupture the capsules therein. The deficiencies of this arrangement are the same as with Smith.

Another problem with the above IV bags, and with other conventional IV bags, is that of pressure equalization. More particularly, because the IV bags are hermetically sealed, a reduction in internal pressure develops as the liquid medicament flows from the IV bag. This change in pressure may have an effect on the rate of flow of the liquid medicament from the IV bag. Thus, the patient may not receive the proper dosage of the drug.

In this regard, U.S. Pat. No. 3,193,993 to Barton et al. discloses a partially rigid bottle with a semi-permeable membrane provided for the equalization of internal pressure with the external atmosphere. This is provided because the container is only slight deformable or collapsible, and it is therefore necessary to provide for the entry of air to permit the contents to flow out through the administration set. In this Patent, a side wall of the container is provided with an indented area, and a disc of resealing rubbery material is affixed to the indented area and provides for the insertion of the spike of an air inlet and filter device for such pressure equalization. The Barton et al. device suffers from two deficiencies in that this container is undesirably opaque, and extensive effort and cost is expended in attempting to make it sufficiently transparent, and the filling and sterilizing procedure is difficult to accomplish owing to the risk of container deformation.

U.S. Pat. No. 4,356,012 to Hofstetter relates to urinary drainage containers. With this Patent, a vent opening is provided and a hydrophobic filter which permits the exit of air from the bag but does not permit liquid to pass through the filter, is sealed against an inner surface of the container. The filter is sealed to the container or bag wall by two anchoring areas, each of which is of a rectangular shape and which extends about the periphery of an area of the container wall defining the vent openings. The purpose of such vent openings, however, is to vent air from the urinary drainage bag to permit the bag to become filled with urine.

OBJECTS AND SUMMARY OF THE INVENTION

Accordingly, it is an object of the present invention to provide a medicament container which avoids the difficulties and problems encountered with conventional devices.

More particularly, it is object of the present invention to provide a medicament container which provides for pressure equalization of the air within the container with the external atmosphere.

It is another object of the present invention to provide a medicament container in which the rate of flow of liquid medicament from the container remains substantially constant.

It is still another object of the present invention to provide a medicament container in which air is forced into the container at a desired rate to control the flow of liquid medicament from the container.

In accordance with an aspect of the present invention, a substantially non-collapsible medicament container is provided and includes a main body defining a chamber for containing the medicament in liquid form, the main body having an upper portion and a lower portion; an opening formed in the upper portion; a liquid impervious, gas permeable membrane secured to the upper portion of the main body in sealing relation to the opening; and a rupturable exit port formed in the lower portion of the main body.

The above and other objects, features and advantages of the present invention will become readily apparent from the following detailed description thereof which is

DETAILED DESCRIPTION OF THE PREFERRED EMBODIMENTS

Figure 1:
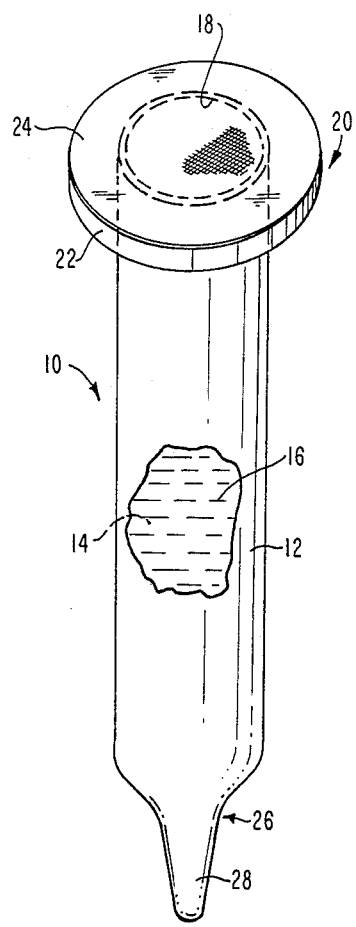
FIG. 1 is a perspective view of a medicament container according to a first embodiment of the present invention.

Referring to the drawings in detail, and initially to FIG. 1 thereof, a medicament container 10 according to a first embodiment of the present invention includes a substantially non-collapsible main body 12 defining a chamber 14 therein which contains a liquid medicament 16. As shown, main body 12 is formed in an elongated cylindrical configuration. However, the present invention is not limited by this configuration, and main body 12 can take any other suitable shapes.

Preferably, main body 12 is a rigid plastic container made of a medical grade molding resin, such as polypropylene. The volume of main body 12 may range, for example, from 50 cc or 100 cc, and may include capacities on the order of 500 cc or 1000 cc. The use of polypropylene is particularly advantageous herein, as polypropylene may be heat sealed to itself and possesses improved clarity and rigidity that is desired with IV containers.

An opening 18 is formed at the upper end 20 of main body 12, and an annular flange 22 surrounds opening 18 at upper end 20. In accordance with the present invention, in order to obtain pressure equalization within chamber 14, a liquid impervious, gas permeable membrane 24 is secured to annular flange 22 in covering and sealing relation with respect to opening 18.

Membrane 24 may be made of any suitable material, such as polypropylene, nylon, polysulfone or the like, having a pore size of, for example, 0.02 um, 1 um or the like. Membrane 24 can be attached to annular flange 22 by any suitable means, such as heat sealing or with an adhesive such as polyurethane. Membrane 24 could also be incorporated into a solid support or frame (not shown) which in turn, may be attached to flange 22. In addition, membrane 24 can be provide with additional rigidity by means of a re-enforcing support or mesh (not shown).

At the opposite lower end 26, container 12 tapers down to a standard sized exit port 28 which can be manufactured with a rupturable closure incorporated therein or could be independently sealed with plastic or a similar composition. Sealed exit port 28 is rupturable in order to cause the liquid medicament 16 to flow out of main body 12. In the present Application, rupture may be accomplished by any manner of providing an opening in exit port 28, such as puncturing, tearing, cutting or the like. Specifically, exit port 28 could be ruptured by the thrust therethrough of the spike from a standard IV set (not shown). Further, a segment of conforming plastic or rubber tubing may extend over lower end 26 past exit port 28, and over to the spike of the IV set to assure that leakage at such joints is minimized.

In order to fill medicament container 10, main body 12 is first filled with liquid medicament 16 through opening 18. Thereafter, membrane 24 either alone or in a supported structure as discussed above, is affixed to annular flange 22. Then, during subsequent use, exit port 28 is ruptured so that liquid medicament 16 flows out of main body 12. During such outflow, membrane 24 provides pressure equalization between the air within chamber 14 and the external atmosphere, so as to ensure a steady rate of flow of the liquid medicament 16 from main body 12.

Figure 2:
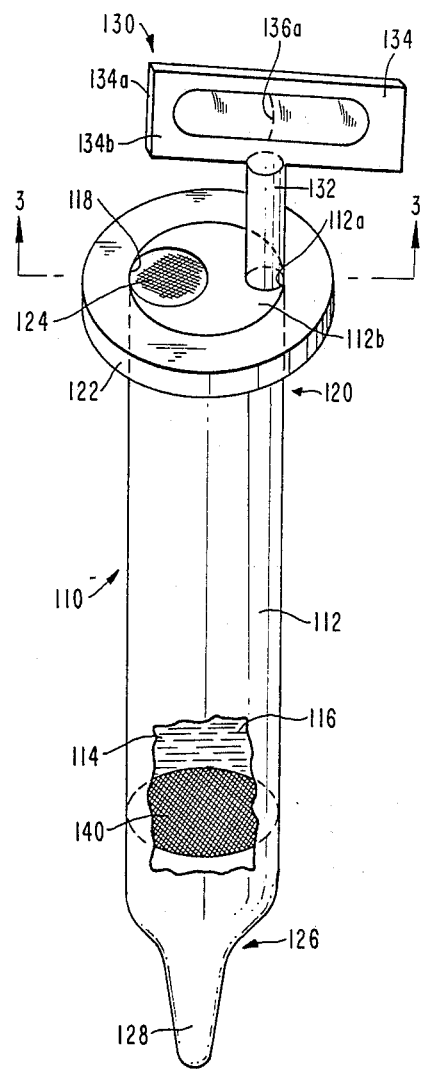
FIG. 2 is a perspective view of a medicament container according to a second embodiment of the present invention.

Referring now to FIG. 2, there is shown a medicament container 110 according to a second embodiment of the present invention, in which elements identical to those identified with respect to medicament container 10 of FIG. 1 are identified by the same reference numerals, augmented by 100, and a detailed description thereof will be omitted herein for the sake of brevity.

Figure 3:
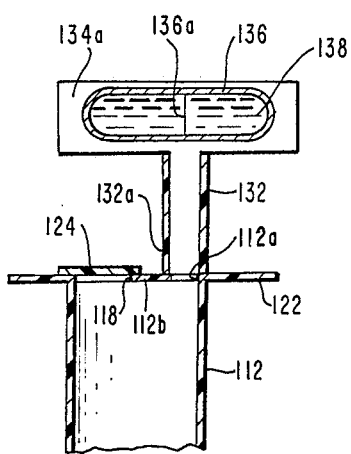
FIG. 3 is a cross-sectional view of a portion of the medicament container of FIG. 2, taken along line 3—3 thereof.
Figure 5:
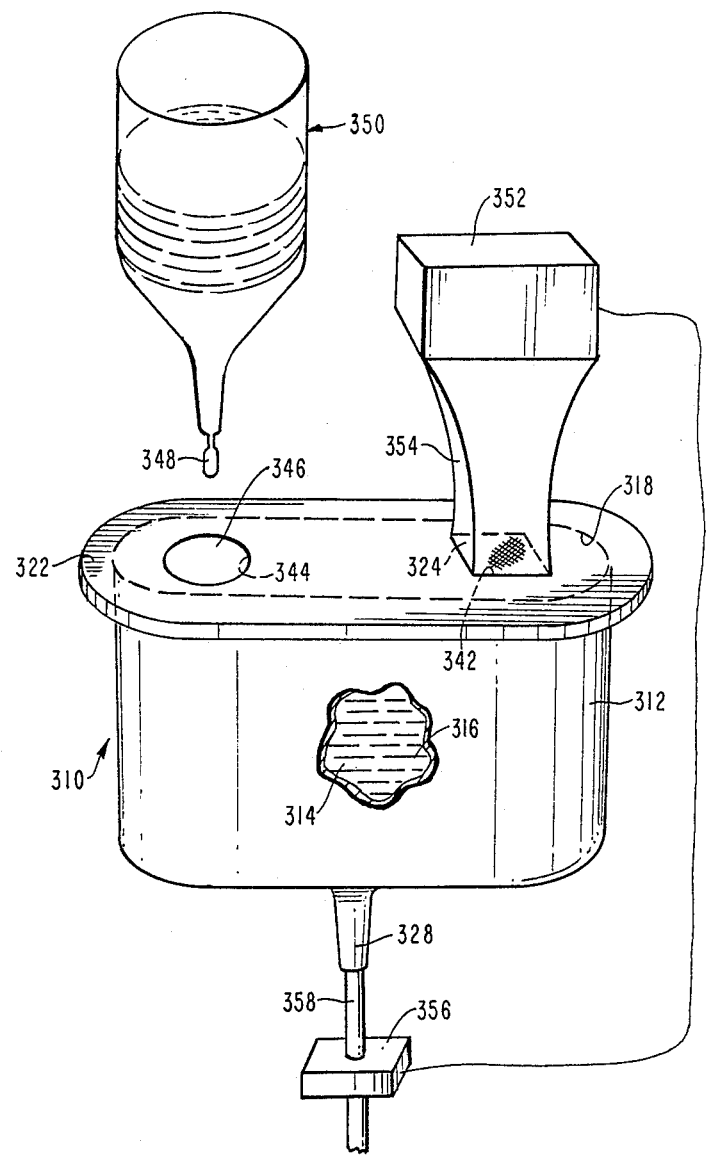
FIG. 5 is a perspective view of a medicament container according to a third embodiment of the present invention.

The embodiment of FIGS. 2, 3 and 5 are designed for use with unstable drugs at room temperature. In these embodiments, the container/dispenser assembly includes a secondary container for the unstable medicament that is adapted for fluid-tight engagement with the main body 112 to permit the unstable drug to be stored in isolation until just prior to delivery. Accordingly, in the embodiment illustrated in FIGS. 2 and 3, a T-shaped connector 130 is connected at upper end 120 of medicament container 110. T-shaped connector 130 includes a vertically oriented tubular leg 132 having its open, lower end 132a extending through an aperture 112a in the top 112b of main body 112 and into fluid communication with chamber 114. As shown in FIG. 3, this can be accomplished by adhering the lower end 132a of tubular leg 132, on top 112b of main body 112, in surrounding relation to aperture 112a, or alternatively, this assembly can be prepared by integrally forming tubular leg 132 with top 112b of main body 112. Alternatively, tubular leg 132 can be adapted to register with a connection conduit or the like (not shown) which is integrally formed with main body 112 or can be inserted through a side wall of main body 112.

T-shaped connector 130 also includes an ampule or capsule container 134 which can be formed of a flexible medical grade plastic tubing constructed in two halves 134a and 134b, which are heat sealed to each other. Alternatively, container 134 may be a singular tube which is affixed to the stem of a second tube to form the "T" shape, after which the ampule may be inserted therein and the ends of the tube thereafter sealed. Before heat sealing halves 134a and 134b together, an ampule or capsule 136 is placed between halves 134a and 134b so as to be sealably enclosed between halves 134a and 134b, but with the center of ampule container 134 in fluid communication with tubular leg 132.

With this embodiment, only the diluent and adducts 116 would be enclosed within chamber 114 of the main body 112. The drug 138 to be mixed therewith is stored in ampule 136 made of a gas and vapor impermeable material, such as glass, aluminum or the like. When it is desired to mix the drug with the diluent and adducts, container 134 is bent, squeezed or the like, in order to open ampule 136. In this regard, ampule 136 may be provided with a perforated or notched center line 136a in order to aid in the opening thereof. In particular, the ampule breaks cleanly along the center line 136a so that the ampule halves remain intact and stay in the tube, while their contents drop down as desired. The drug 138 within ampule 136 thereby falls through tubular leg 132 into chamber 114 to mix with the liquid diluent and adducts therein. Main body 112 can be shaken in order to enhance the mixing.

It will be appreciated that, with this embodiment, portions of crushed or bent ampule 136 may still result and may also fall through tubular leg 132. In order to prevent any such small stray pieces of ampule 136 from passing through exit port 128, a screen 140 can be provided at the lower portion 126 of main body 112.

Further, top 112b is provided with a second opening 118 in communication with chamber 114. A membrane 124, substantially identical to membrane 24 of FIG. 1, is secured to top 112a and annular flange 122 in covering and sealing relation with respect to opening 118. Thus, pressure equalization within chamber 114 is obtained.

Figure 4:
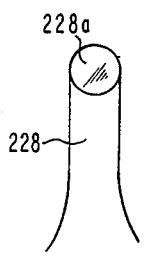
FIG. 4 is a perspective view showing a modification of the exit port of the medicament containers of FIGS. 1 and 2.

Although exit ports 28 and 128 have been shown as having a rounded end, according to a modification of the present invention, an exit port 228 as shown in FIG. 4 can be formed with a flat end 228a which makes it relatively easy to puncture the same in order to remove the liquid medicament from the medicament container.

Referring now to FIG. 5, there is shown another embodiment of the present invention in which elements similar to those in the embodiment of FIG. 1 are identified by the same reference numerals, augmented by 300, and in a detailed description thereof will be omitted herein for the sake of brevity.

As shown therein, medicament container 310 has an elongated, oblong cross-sectional configuration. With this embodiment, annular flange 322 is formed with two spaced openings 342 and 344. Liquid impervious, gas permeable membrane 324 is secured to annular flange 322 in sealing relation to opening 342, and thereby does not cover the entire surface of the annular flange as in the embodiments of FIG. 1. An elastomeric, puncturable, sealing material 346 is secured to annular flange 322 in sealing relation to second opening 344. Sealing material 346 is intended to be punctured by the tapered end of a nozzle 348 secured to the delivery end of a resilient bottle 350 or other container which contains a medicament to be added to chamber 314. In the illustrated embodiment, tapered end 348 may terminate in a break-away tab or tip seal 352 that when fractured and removed, exposes a fluid passageway, not shown, that in turn permits the medicament to flow from bottle 350 into container 310 when end 348 is thrust through sealing material 346 into fluid-tight engagement therewith. In this regard, the embodiment of FIG. 5 is similar to that of FIG. 2, having particular applicability for use with unstable drugs.

As the fluid level in the IV container drops during fluid administration, some slowing of flow may occur. When this occurs with known IV bags, etc., peristaltic pumps have been used to regulate flow. In the present case, although peristaltic pumps are useful, it is perferred from the standpoint of simplicity and economy to use a small blower assembly in association with a flow or pressure sensor. Accordingly, a small blower or fan 352 is connected through a conduit 354 to membrane 324, as shown. Blower 352 forces air through conduit 354 and membrane 324, and as a result, flow through exit port 328 is maintained at a substantially constant rate.

In order to absolutely ensure such constant rate of flow of liquid medicament 316 through exit port 328, a pressure or flow sensing device 356 is connected through a conduit 358 to outlet port 328 and senses the rate of flow of liquid medicament 316 therethrough. If the rate of flow is insufficient, such sensing device 356 increases the power to blower 352, whereby blower 352 forces a greater supply of air through membrane 324 to increase the rate of flow. On the other hand, if the rate of flow resulting from the operation of blower 352 is too great, pressure sensing device 356 shuts off or reduces the power to blower 352.

Having described specific preferred embodiments of the invention with reference to the accompanying drawings, it will be appreciated that the present invention is not limited to those precise embodiments, and that various changes and modifications can be effected therein by one of ordinary skill in the art without departing from the scope or spirit of the invention as defined in the appended claims.

I claim:

1. A disposable container/dispenser assembly for the extended storage and direct intravenous administration of a medicament comprising;
   a substantially non-collapsible main body defining a chamber for containing said medicament in liquid form, said main body being prepared from a medical grade polypropylene-containing molding resin and having an upper portion and a lower portion;
   pressure equalizing means consisting essentially of a liquid impervious, gas permeable membrane prepared from a material selected from the group consisting of polypropylene, nylon, and polysulfone, said membrane permanently attached to the upper portion of said main body; and an exit port consisting of a tube extending from the lower portion of said main body and having a rupturable closed end.

2. A medicament container/dispenser assembly according to claim 1; further including an opening formed in the upper portion of said main body in spaced relation to said pressure equalizing means, and an elastomeric, puncturable, sealing material secured to the upper portion of said main body in sealing relation to opening.

3. A medicament container/dispenser assembly according to claim 2; further including a secondary container for holding and dispensing an unstable drug in diluted form, and fluid-tight connector means for joining said secondary container and said main body to permit said unstable drug to be placed in solution in preparation for administration.

4. A medicament container/dispenser assembly according to claim 3; wherein said secondary container and said connector means are adapted to communicate with said main body through said sealing material.

5. A medicament container/dispenser assembly according to claim 4; wherein said connector means comprises an integral spout extending from said secondary container defining a needle-like point at the free end thereof having a break-away tip seal to retain the medicament in said secondary container, said connector means adapted to be thrust into fluid-tight engagement with said sealing material after said break-away tip seal is removed.

6. A medicament container/dispenser assembly according to claim 1; wherein said lower portion has a tapered configuration, ending in said exit port.

7. A medicament container/dispenser assembly according to claim 6; wherein said lower portion terminates in a flat end which forms said exit port.

8. A medicament container/dispenser assembly according to claim 1; further including connector means in fluid communication with said chamber for containing a drug.

9. A medicament container/dispenser assembly according to claim 8; wherein said connector means includes a T-shaped connector having a first leg in fluid communication with said chamber through said opening, and a deformable ampule container in fluid communication with said leg for containing a medicament ampule therein.

10. A medicament container/dispenser assembly according to claim 9; further including screen means positioned in said chamber to prevent pieces of said ampule from passing through said exit port.

11. A medicament container according to claim 1; further including a conduit positioned adjacent said membrane at the upper section of said main body, and blower means for supplying forced air to said membrane through said conduit.

12. A medicament container/dispenser assembly according to claim 11; further including sensing means for sensing pressure of said liquid medicament from said exit port and for controlling said blower means in response thereto.

13. A medicament container/dispenser assembly according to claim 11; further including sensing means for sensing flow of said liquid medicament from said exit port and for controlling said blower means in response thereto.

* * * * *